(12) United States Patent
Satoh et al.

(10) Patent No.: US 6,391,821 B1
(45) Date of Patent: May 21, 2002

(54) OXIDATION CATALYST

(75) Inventors: Yuuichi Satoh, Suita; Jun Tatsumi, Ikoma; Toshiya Iida, Suita; Toshio Hayashi, Kobe, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/334,379

(22) Filed: Jun. 16, 1999

(30) Foreign Application Priority Data

Jun. 17, 1998 (JP) .......................................... 10-169724
Apr. 7, 1999 (JP) .......................................... 11-100261

(51) Int. Cl.$^7$ ........................... B01J 23/00; B01J 23/58; B01J 23/70; B01J 23/42; B01J 23/16
(52) U.S. Cl. ....................... 502/300; 502/303; 502/328; 502/329; 502/333; 502/335; 502/336; 502/337; 502/338; 502/339; 502/330; 502/353
(58) Field of Search ................................. 502/330, 333, 502/339, 328, 329, 335–338, 303, 353, 300

(56) References Cited

U.S. PATENT DOCUMENTS

| 3,655,747 | A | * | 4/1972 | Sennewald et al. | ..... | 260/530 R |
| 3,822,308 | A | * | 7/1974 | Kronig et al. | ........... | 260/497 A |
| 4,499,298 | A | * | 2/1985 | Scheben et al. | ............ | 560/241 |
| 5,347,046 | A | * | 9/1994 | White et al. | ................. | 560/245 |
| 5,413,984 | A | * | 5/1995 | Marecot et al. | ............. | 502/333 |
| 5,422,329 | A | | 6/1995 | Wirtz et al. | .................. | 502/328 |
| 5,559,071 | A | * | 9/1996 | Abel et al. | .................... | 502/326 |
| 5,623,090 | A | | 4/1997 | Haruta et al. | ............... | 568/360 |
| 5,693,586 | A | * | 12/1997 | Nicolau et al. | ............. | 502/330 |
| 5,700,753 | A | | 12/1997 | Wang et al. | ................. | 502/330 |
| 6,022,823 | A | * | 2/2000 | Augustine et al. | .......... | 502/243 |

FOREIGN PATENT DOCUMENTS

| EP | 0 654 301 A1 | 5/1995 |
| EP | 0 709 360 A1 | 5/1996 |
| GB | 1328058 | 8/1973 |
| JP | 62-273927 | 11/1987 |
| JP | 63-174950 | 7/1988 |
| JP | 8-231466 | 9/1996 |
| WO | WO 97/33690 | 9/1997 |

OTHER PUBLICATIONS

"Vapor–phase Oxidative Acetoxylation of Toluene on Palladium–based Bimetallic Catalysts". (M. Matsukata, et al. SEKIYU GAKKAISHI, 37, (4), 428–434, 1994, Nov. 1993.
"Oxidative acetoxylation of p–xylene over supported–Pd catalysts: Effect of Au addition on catalytic activity, selectivity and stability." (M. Matsukata, et al., 78$^{th}$ CATSJ Meeting Abstracts: No. 5 B01, Catalyst vol. 38, No. 6, 498–501, 1996) [In Japanese with translation of relevant passages.] Month Not Avail.

* cited by examiner

Primary Examiner—Mark L. Bell
Assistant Examiner—Patricia L. Hailey
(74) Attorney, Agent, or Firm—Dike, Bronstein, Roberts & Cushman IP Group; David G. Colin; David A. Tucker

(57) ABSTRACT

An oxidation catalyst according to the present invention is prepared, for example, by heat processing a gold compound at 150° C. to 80° C., yielding ultrafine gold particles, which are then mixed with a palladium compound and a compound containing at least one element selected from the group consisting of alkaline metals and the elements of Groups IIA, IIIA, VIA, IIB, VB, and VIII of the Periodic Table. By an oxidation reaction between a benzyl compound such as p-xylene and a carboxylic acid such as acetic acid in the presence of oxygen and the oxidation catalyst prepared as above, a benzyl ester such as p-methylbenzyl acetate or p-xylylene diacetate can be produced. Consequently, it is possible to provide an oxidation catalyst suitable for use in industrially producing the foregoing benzyl esters, a method of preparing the foregoing oxidation catalyst, and a method of producing the foregoing benzyl esters efficiently and at low cost.

10 Claims, No Drawings

US 6,391,821 B1

OXIDATION CATALYST

FIELD OF THE INVENTION

The present invention relates to an oxidation catalyst suitable for use in producing a benzyl ester such as p-methylbenzyl acetate or p-xylylene diacetate by reacting a benzyl compound such as p-xylene with a carboxylic acid such as acetic acid, and relates to a method of preparing such an oxidation catalyst and a method of producing such a benzyl ester.

BACKGROUND OF THE INVENTION

Aromatic esters (benzyl esters) such as p-methylbenzyl acetate and p-xylylene diacetate are generally used as starting materials for synthetic resins such as polyester resin, as chemical substances such as aromatics and solvents, and as starting materials for producing such chemical substances. With regard to methods of producing such aromatic esters, Japanese Unexamined Patent Publication No. 63-174950/1988 (Tokukaisho 63-174950, published on Jul. 19, 1988), for example, discloses a method of producing p-methylbenzyl acetate and p-xylylene diacetate by reacting p-xylene and acetic acid in the presence of oxygen, using a palladium-bismuth compound and/or a palladium-lead compound as a catalyst. Again, Japanese Unexamined Patent Publication No. 62-273927/1987 (Tokukaisho 62-273927, published on Nov. 28, 1987), for example, discloses a method of producing p-xylylene diacetate by reacting p-xylene and acetic acid in the presence of oxygen, using a catalyst containing palladium and bismuth.

Further, Japanese Unexamined Patent Publication No. 8-231466/1996 (Tokukaihei 8-231466, published on September 10, 1996), for example, discloses a method of producing p-xylylene diacetate by reacting p-xylene and acetic acid in the presence of oxygen, using a catalyst made of palladium and gold on a support.

However, the activity of catalysts disclosed in the foregoing Japanese Unexamined Patent Publication Nos. 63-174950/1988 and 62-273927/1987 is low (the turnover factor per unit of palladium per unit time being around 15), and thus, in order to improve production efficiency, it is necessary to use a large amount of catalyst in comparison to the reaction substrate p-xylene. In other words, a large amount of palladium, which is a precious metal, must be used. Further, the palladium may elute into the reaction solution during the reaction, and in this case, activity of the catalyst is further decreased, and it becomes necessary to separate and recover the eluted palladium. For these reasons, the foregoing catalyst cannot be said to be suited to industrial production methods.

Further, the catalyst disclosed in Japanese Unexamined Patent Publication No. 8-231466/1996 also has low activity, and thus in order to improve production efficiency, it is necessary to use a large amount of catalyst in comparison to the reaction substrate p-xylene. Accordingly, neither can the foregoing catalyst be said to be suited to industrial production methods.

In other words, because of their low catalytic activity, the foregoing conventional catalysts are unsuitable for industrial production methods, and thus have the drawback that benzyl ester cannot be produced efficiently and at low cost.

SUMMARY OF THE INVENTION

It is an object of the present invention to provide an oxidation catalyst suitable for use in producing a benzyl ester such as p-methylbenzyl acetate or p-xylylene diacetate by reacting a benzyl compound such as p-xylene with a carboxylic acid such as acetic acid in the presence of oxygen, and to provide a method of preparing such an oxidation catalyst and a method of producing such a benzyl ester efficiently and at low cost.

The inventors of the present invention conducted assiduous investigation in connection with oxidation catalysts for oxidizing benzyl compounds, methods of preparing such oxidation catalysts, and methods of producing benzyl esters. As a result, the inventors found that an oxidation catalyst containing palladium, ultrafine gold particles, and at least one element selected from the group consisting of alkaline metals and the elements of Groups IIA, IIIA, VIA, IIB, VB, and VIII of the Periodic Table had high catalytic activity in a reaction for producing a benzyl ester from a benzyl compound and a carboxylic acid in the presence of oxygen, i.e., that such an oxidation catalyst was suitable for industrial production of a benzyl ester. The inventors then confirmed that by using the foregoing oxidation catalyst it was possible to industrially produce a benzyl ester efficiently and at low cost, thus completing the present invention.

In order to attain the foregoing object, an oxidation catalyst according to the present invention is a catalyst for oxidation of a benzyl compound, and contains palladium, ultrafine gold particles, and at least one element selected from the group consisting of alkaline metals and the elements of Groups IIA, IIIA, VIA, IIB, VB, and VIII of the Periodic Table. Further, an oxidation catalyst according to the present invention may be characterized in that the element selected from the foregoing group is at least one element selected from the group consisting of bismuth, molybdenum, iron, nickel, zinc, lanthanum, an alkaline earth metal, and an alkaline metal. Further, an oxidation catalyst according to the present invention may be characterized in that the ultrafine gold particles are supported on a support.

Each of the foregoing oxidation catalysts has higher catalytic activity than conventional catalysts, and is suitable for use in an industrial production method. Consequently, with any of the foregoing structures, an oxidation catalyst can be provided which is suitable for use in producing a benzyl ester such as p-methylbenzyl acetate or p-xylylene diacetate by reacting a benzyl compound such as p-xylene with a carboxylic acid such as acetic acid.

Further, in order to attain the foregoing object, a method of preparing an oxidation catalyst according to the present invention includes the steps of: (a) heat processing a gold compound at 150° C. to 800° C. to obtain ultrafine gold particles; and (b) mixing the ultrafine gold particles obtained in step (a) with a palladium compound and a compound containing at least one element selected from the group consisting of alkaline metals and the elements of Groups IIA, IIIA, VIA, IIB, VB, and VIII of the Periodic Table. Further, in order to attain the foregoing objects, another method of preparing an oxidation catalyst according to the present invention includes the steps of: (a) heat processing a gold compound and a palladium compound at 150° C. to 800° C. to obtain a mixture containing ultrafine gold particles and palladium; and (b) mixing the mixture obtained in step (a) with a compound containing at least one element selected from the group consisting of alkaline metals and the elements of Groups IIA, IIIA, VIA, IIB, VB, and VIII of the Periodic Table.

Using either of the foregoing methods, it is possible to prepare an oxidation catalyst having higher catalytic activity than conventional catalysts. Consequently, with any of the foregoing structures, an oxidation catalyst can be provided which is suitable for use in producing a benzyl ester such as p-methylbenzyl acetate or p-xylene diacetate by reacting a benzyl compound such as p-xylene with a carboxylic acid such as acetic acid.

Further, in order to attain the foregoing object, a method of producing benzyl ester according to the present invention is a method of producing benzyl ester by an oxidation reaction between a benzyl compound and a carboxylic acid in the presence of oxygen and an oxidation catalyst containing palladium, ultrafine gold particles, and at least one element selected from the group consisting of alkaline metals and the elements of Groups IIA, IIIA, VIA, IIB, VB, and VIII of the Periodic Table. Another method of producing benzyl ester according to the present invention is characterized in that the foregoing oxidation reaction is carried out in a liquid phase.

With the foregoing production method, it is possible to industrially produce benzyl ester efficiently and at low cost. For example, a benzyl ester such as p-methylbenzyl acetate or p-xylylene diacetate can be industrially produced, efficiently and at low cost, from p-xylene as the benzyl compound.

Additional objects, features, and strengths of the present invention will be made clear by the description below. Further, the advantages of the present invention will be evident from the following explanation.

DESCRIPTION OF THE EMBODIMENTS

The oxidation catalyst for oxidation of a benzyl compound according to the present invention (hereinafter referred to simply as the "catalyst") contains palladium, ultrafine gold particles, and at least one element selected from the group consisting of alkaline metals and the elements of Groups IIA, IIIA, VIA, IIB, VB, and VIII of the Periodic Table. Further, the method of preparing the catalyst according to the present invention includes the steps of (a) heat processing a gold compound at 150° C. to 800° C. to obtain ultrafine gold particles; and (b) mixing the ultrafine gold particles obtained in step (a) with a palladium compound and a compound containing at least one element selected from the group consisting of alkaline metals and the elements of Groups IIA, IIIA, VIA, IIB, VB, and VIII of the Periodic Table (hereinafter referred to as the "third compound"). Alternatively, the method of preparing the catalyst according to the present invention includes the steps of (a) heat processing a gold compound and a palladium compound at 150° C. to 800° C. to obtain a mixture containing ultrafine gold particles and palladium; and (b) mixing the mixture obtained in step (a) with the third compound. In the present invention, "ultrafine particles" refers to particles having diameters on the nanometer (nm) order. Further, in the present invention, "the elements of Group VIII of the Periodic Table" will not include palladium.

The palladium compound to be used in preparing the catalyst according to the present invention is not particularly limited; specific examples include metallic palladium, palladium oxide, palladium nitrate, palladium sulfate, palladium acetate, ammonium hexachloropalladate (IV), sodium hexachloropalladate (IV), potassium hexachloropalladate (IV), ammonium tetrachloropalladate (II), sodium tetrachloropalladate (II), potassium tetrachloropalladate (II), potassium tetrabromopalladate (II), potassium tetracyanopalladate (II), palladium chloride, palladium bromide, palladium iodide, chlorocarbonyl palladium, potassium dinitrosulfite palladate (II), dinitrodiamine palladium, tetraammine palladium chloride, tetraammine palladium nitrate, cis-dichlorodiamine palladium, trans-dichlorodiamine palladium, bis-triphenylphosphine palladium dichloride, and dichloro(ethylenediamine) palladium. A single palladium compound may be used alone, or two or more may be used in combination. Among the palladium compounds listed above, those which are water-soluble are preferable; palladium nitrate, palladium sulfate, palladium acetate, palladium chloride, and tetraammine palladium chloride are more preferable; and palladium acetate and tetraammine palladium chloride are especially preferable. Incidentally, the palladium compound may be a hydrate.

The gold compound to be used in preparing the catalyst according to the present invention is not particularly limited, provided it is water-soluble; specific examples include complexes such as tetrachloroauric (III) acid ($H(AuCl_4)$), sodium tetrachloroaurate (III) ($Na(AuCl_4)$), potassium dicyanoaurate (I) ($K(Au(CN)_2)$), and gold (III) diethylamine trichloride (($(C_2H_5)_2NH.(AuCl_3)$)); and gold (I) cyanide (AuCN). A single gold compound may be used alone, or two or more may be used in combination. Among the gold compounds listed above, tetrachloroauric (III) acid is especially preferable. Incidentally, the gold compound may be a hydrate.

The third compound to be used in preparing the catalyst according to the present invention is not particularly limited, provided it contains at least one element selected from the group consisting of alkali metals and the element of Groups IIA, IIIA, VIA, IIB, VB, and VIII of the Periodic Table; more preferably, at least one element selected from the group consisting of bismuth, molybdenum, iron, nickel zinc, lanthanum, alkaline earth metals, and alkali metals.

Specific examples of the third compound include, but are not limited to, bismuth compounds such as bismuth acetate, bismuth acetate oxide, bismuth fluoride, bismuth chloride, bismuth bromide, bismuth iodide, bismuth oxide, bismuth hydroxide, bismuth oxychloride, bismuth nitrate, and bismuth carbonate basic; molybdenum compounds such as molybdic acid, sodium molybdate, molybdenum boride, molybdenum chloride, molybdenum oxide, phosphomolybdic acid, silicomolybdic acid, molybdenum oxide acetylacetonate, and molybdenum hexacarbonyl; iron compounds such as iron nitrate, iron sulfate, iron phosphate, iron chloride, iron bromide, iron acetate, iron oxalate, and iron acetylacetonate; nickel compounds such as nickel acetate, nickel chloride, nickel bromide, nickel carbonate, nickel oxide, nickel hydroxide, nickel nitrate, nickel sulfate, nickel cyanate, and nickel acetylacetonate; zinc compounds such as zinc acetate, zinc chloride, zinc bromide, zinc iodide, zinc carbonate, zinc oxide, zinc nitrate, zinc sulfate, zinc phosphate, zinc cyanate, and zinc acetylacetonate; lanthanum compounds such as lanthanum acetate, lanthanum oxalate, lanthanum chloride, lanthanum bromide, lanthanum carbonate, lanthanum oxide, lanthanum nitrate, lanthanum sulfate, and lanthanum acetylacetonate; alkaline metal compounds such as acetates, nitrates, sulfates, halides, and oxides of alkaline metals, and alkaline metal acetylacetonates; and alkaline earth metal compounds such as acetates, nitrates, sulfates, halides, and oxides of alkaline earth metals, and alkaline earth metal acetylacetonates.

A single third compound may be used alone, or two or more may be used in combination. Among the examples of the third compound listed above, bismuth compounds, alkali metal compounds, and alkaline earth metal compounds are preferable; and bismuth acetate, bismuth acetate oxide, bismuth nitrate, potassium acetate, sodium acetate, cesium acetate, potassium nitrate, barium acetate and barium nitrate are especially preferable. Incidentally, the third compound may be a hydrate.

One specific method of obtaining the ultrafine gold particles to be used in the method of preparing the catalyst according to the present invention is to immerse a support in an aqueous solution containing the foregoing gold compound and a surfactant, thereby causing gold precipitate to be deposited onto the support, and then to heat process the support at 150° C. to 800° C. to affix the gold precipitate on the support. Further, one specific method of obtaining the mixture of ultrafine gold particles and palladium to be used in another method of preparing the catalyst according to the present invention is to impregnate a support with an aqueous solution containing the foregoing gold compound, the foregoing palladium compound, and a surfactant, thereby causing gold precipitate and palladium precipitate to be deposited onto the support, and then to heat process the support at 150° C. to 800° C. to affix the respective precipitates on the support. In other words, the ultrafine gold particles are preferably supported by a support.

The foregoing support is not particularly limited, provided it is an inorganic substance, preferably a porous inorganic substance. Specific examples of inorganic substances which can be used for the support include titanium oxide (titania), zirconium oxide (zirconia), silicon oxide (silica), aluminum oxide (alumina), silica.alumina, silica.titania, zeolite, silica gel, magnesium oxide (magnesia), silica-magnesia, activated carbon, clay, bauxite, diatomaceous earth, and quartzite. For the support, one of the foregoing inorganic substances may be used alone, or two or more may be used in combination. In the present invention, the support preferably includes at least one inorganic substance selected from the group consisting of titanium oxide, zirconium oxide, and aluminum oxide. In the present invention, "includes titanium oxide" means that the support itself is made of inorganic substances including titanium oxide, or that a support made of inorganic substances other than titanium oxide supports titanium oxide on its surface. The crystal structure of the titanium oxide is not particularly limited, but is preferably amorphous or anatase. Incidentally, the inorganic substances such as titanium oxide, zirconium oxide, silicon oxide, and aluminum oxide may be hydrates.

Further, when titanium oxide is supported on the surface of the support, it is especially preferable for the titanium oxide to be dispersed on the surface thereof in the form of so-called islets. Incidentally, the titanium oxide may also be placed on the surface of the support by an operation such as coating. Further, the support may support other inorganic substances in addition to the titanium oxide.

The specific surface area of the support is not particularly limited, but is preferably no less than 50 m$^2$/g. If the specific surface area is less than 50 m$^2$/g, the quantity of ultrafine gold particles affixed may be reduced. In other words, the activity of the catalyst may be reduced. Further, when the support is a molded object, the shape, size, and method of molding are not particularly limited.

The quantity of the gold compound used depends on the type, specific surface area, shape, and quantity of the support, but is preferably a quantity such that concentration of the gold compound in the foregoing aqueous solution is in a range from 0.01 millimoles/L to 10 millimoles/L. A concentration of less than 0.01 millimoles/L is not preferable because in this case the quantity of gold precipitate deposited is too small. Further, a concentration of more than 10 millimoles/L is not preferable because in this case the gold is likely to aggregate, and thus the particle size of the deposited gold precipitate, i.e., of the gold particles to be affixed on the support, becomes too large, making it impossible to produce ultrafine particles. When the catalyst does not contain ultrafine gold particles, its catalytic activity is greatly reduced.

The foregoing surfactant is not particularly limited; specific examples include anionic surfactants such as long-chain alkylsulfonic acid and salts thereof, long-chain alkylbenzenesulfonic acid and salts thereof, and long-chain alkylcarboxylic acid and salts thereof; cationic surfactants such as long-chain alkyl quaternary ammonium salts; and nonionic surfactants such as polyalkylene glycol and polyoxyethylenenonylphenol. A single surfactant may be used alone, or two or more may be used in combination. Among the examples of surfactants listed above, anionic surfactants and nonionic surfactants are preferable, and anionic surfactants are especially preferable. Further, among anionic surfactants, long-chain alkyl(aryl)sulfonic acids having 8 or more carbon atoms and salts thereof, and long-chain alkyl (aryl)carboxylic acids having 8 or more carbon atoms and salts thereof, are especially preferable.

The quantity of surfactant used is not particularly limited, and may be set according to the types and combination of the surfactant, the gold compound, the palladium compound, and the support, but is preferably a quantity such that concentration of the surfactant in the foregoing aqueous solution is from 0.1 millimoles/L to 10 millimoles/L. Using a concentration of less than 0.1 millimoles/L may lessen the effect to be obtained by adding the surfactant. On the other hand, using more than 10 millimoles/L cannot be expected to obtain an effect much greater than that obtainable with a concentration in the foregoing range, and operations for washing the support with the gold precipitate (and, as the case may be, the palladium precipitate) deposited thereon become troublesome.

The foregoing aqueous solution can easily be prepared by dissolving the gold compound (and, as necessary, the palladium compound) and the surfactant in water, and adjusting the pH thereof. The pH of the aqueous solution is preferably adjusted to within a range of 6 to 10. By adjusting the pH of the aqueous solution to within this range, gold precipitate is produced in the form of ultrafine particles. Incidentally, the method of preparing the aqueous solution is not particularly limited.

In order to adjust the pH of the aqueous solution to within the foregoing range, a compound showing alkalinity may be added as necessary. This alkaline compound is not particularly limited; specific examples include sodium carbonate, potassium carbonate, sodium hydroxide, potassium hydroxide, and ammonia. The alkaline compound may be added in the form of a solid, or may be dissolved in water.

The support is immersed in the foregoing aqueous solution by adding the support to the aqueous solution while stirring. By stirring, the immersed support is dispersed and suspended in the aqueous solution, and the gold precipitate (and, as the case may be, the palladium precipitate) deposited on the surface thereof, i.e. on the support. Specific examples of the gold precipitate include gold hydroxide and ultrafine gold particles. The gold precipitate has a comparatively narrow spread of particle diameters. Incidentally, the method of application to the support is not particularly limited, and methods such as precipitation, ion exchange, impregnation, and deposition may be used.

The temperature at which the gold precipitate is deposited onto the support is preferably around 30° C. to 80° C.

Further, a duration of around 10 minutes to 3 hours is sufficient for deposition. If necessary, the quantity of gold precipitate deposited on the support may be increased by repeating the operations for deposition, to an extent which does not overly increase the particle diameters of the deposited gold precipitate.

By means of the foregoing operations, the gold precipitate (and, as the case may be, the palladium precipitate) is efficiently deposited on the surface of the support, yielding a gold precipitate body. With the foregoing method, since the foregoing aqueous solution contains a surfactant, more gold precipitate can be deposited onto the support than with conventional methods, even, for example, when the support is a molded object, or when the equipotential point of the surface of the support is comparatively low. The quantity of gold contained in the gold precipitate body is preferably high, but a quantity of gold with respect to the total of the gold precipitate body is preferably 0.01% to 20% by weight, or more preferably 0.1% to 5% by weight. If necessary, the gold precipitate body may be washed in water to remove surfactant from the surface thereof.

Then the gold precipitate body is heat processed (specifically, calcined in air) at 150° C. to 800° C., or more preferably at 300° C. to 800° C., yielding a support with ultrafine gold particles, or a mixture of ultrafine gold particles and palladium, affixed thereon (hereinafter collectively referred to as the "ultrafine gold particle body"). Incidentally, when the gold precipitate is gold hydroxide, calcining breaks down the gold hydroxide to form ultrafine gold particles.

The calcining method is not particularly limited. For example, the atmosphere of calcining is not particularly limited, and may be air, an inert gas such as nitrogen, helium, or argon gas, or a reducing gas such as hydrogen gas. Further, the duration of calcination is not particularly limited, and may be set according to the temperature of heating. By calcination, the ultrafine gold particles are firmly affixed to the surface of the support, and in this way the ultrafine gold particle body is prepared. Incidentally, the method of obtaining the ultrafine gold particle body is not limited to the method explained above.

When the ultrafine gold particle body does not include palladium, the catalyst according to the present invention is prepared by mixing the ultrafine gold particle body with the palladium compound and the third compound. When the ultrafine gold particle body includes palladium, the catalyst according to the present invention is prepared by mixing the ultrafine gold particle body with the third compound. Incidentally, even when the ultrafine gold particle body includes palladium, a palladium compound may be mixed therewith as needed.

The method and order of mixing the ultrafine gold particle body, the palladium compound, and the third compound are not particularly limited. Further, the ultrafine gold particle body, the palladium compound, and the third compound may be placed in a reaction device with the starting materials (benzyl compound and carboxylic acid) at the time of production of benzyl ester. In other words, the catalyst according to the present invention may also be prepared by mixing the ultrafine gold particle body and the foregoing compound(s) at the time of production of benzyl ester.

The catalyst prepared according to the foregoing method, i.e., the catalyst according to the present invention, contains palladium, ultrafine gold particles, and at least one element (hereinafter referred to as the "third metallic substance") selected from the group consisting of alkaline metals and the elements of Groups IIA, IIIA, VIA, IIB, VB, and VIII of the Periodic Table.

A ratio among palladium, the ultrafine gold particles, and the third metallic substance, i.e., the composition of the catalyst, is not particularly limited, but palladium preferably makes up 0.001% to 10% by weight, or more preferably 0.1% to 2% by weight, of the catalyst. The ultrafine gold particles preferably make up 0.001% to 10% by weight, or more preferably 0.1% to 5% by weight, of the catalyst. The third metallic substance preferably makes up 0.0001% to 10% by weight, or more preferably 0.001% to 2% by weight, of the catalyst. Proportions of palladium and the ultrafine gold particles less than the respective ranges above are not preferable, because in this case catalytic activity is reduced. With proportions of palladium and the ultrafine gold particles exceeding the respective ranges above, on the other hand, the cost of producing the catalyst is increased, and thus the benzyl ester cannot be produced economically.

Accordingly, the amounts of the palladium compound, the gold compound, and the third compound used in preparing the catalyst may be set so that the composition of the catalyst satisfies the respective ranges above. The catalyst obtained by means of the foregoing preparation method has high catalytic activity, and is suitable for use in oxidation of a benzyl compound.

The benzyl compound used as a starting material in the method of producing benzyl ester according to the present invention is not particularly limited, provided it is a compound having a benzyl group in its molecular structure. Further, the benzyl compound may include a functional group which is inert to the present oxidation reaction. Examples of the benzyl compound include compounds shown by General Formula (1) below.

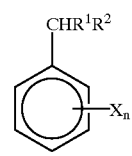

(1)

In General Formula (1), $R^1$ and $R^2$ independently represent a hydrogen atom or an alkyl group; X represents a hydrogen atom, an alkyl group, an aryl group, a hydroxide group, a halogen group, a nitro group, an amino group, an amide group, an alkyloxy group, an aryloxy group, an alkylcarboxyl group, an arylcarboxyl group, an alkylcarbonyl group, an arylcarbonyl group, an alkylcarboxyalkyl group, or an arylcarboxyalkyl group; and n is an integer from 1 to 5 representing the number of X.

Specific examples of the benzyl compound include alkylbenzenes such as toluene, ethylbenzene, n-propylbenzene, isopropylbenzene, n-butylbenzene, sec-butylbenzene, and trimethylbenzene; o-, m-, and p-dialkylbenzenes such as xylene, ethyltoluene, n-propyltoluene, isopropyltoluene, n-butyltoluene, and sec-butyltoluene; aryl substituted alkylbenzenes such as 4,4'-dimethylbiphenyl; o-, m-, and p-hydroxy substituted alkylbenzenes such as cresol; o-, m-, and p-halogen substituted alkylbenzenes such as chlorotoluene; nitro group substituted alkylbenzenes such as o-, m-, and p-nitrotoluene; o-, m-, and p-amino group substituted alkylbenzenes such as methylaniline; o-, m-, and p-amide group substituted alkylbenzenes such as methylbenzamide; o-, m-, and p-alkyloxy substituted alkylbenzenes such as methylanisole; o-, m-, and p-aryloxy substituted alkylbenzenes such as phenoxytoluene; o-, m-, and p-carboxy substituted alkylbenzenes (tolyl carboxylate esters) such as tolyl acetate, tolyl propionate, tolyl butanate, and tolyl benzoate; o-, m-, and p-carbonyl substituted alkylbenzenes such as methylacetophenone and methylbenzophenone; and o-, m-, and p-carboxyalkyl substituted alkylbenzenes such as methylbenzyl acetate. Among the examples of the benzyl compound listed above, alkylbenzene, dialkylbenzene, and carboxyalkyl substituted alkylbenzene are preferable, and o-, m-, and p-xylene and o-, m-, and p-methylbenzyl acetate are especially preferable.

In the present invention, benzyl compounds will also include compounds having a condensed ring or a heterocyclic ring in place of the benzene ring (benzyl group) shown in General Formula (1) above, such as methyl naphthalene, dimethyl pyridine, etc.

The carboxylic acid used as a starting material in the method of producing benzyl ester according to the present invention is not particularly limited, but a monocarboxylic acid is suitable. Specific examples include alkyl carboxylic acids such as acetic acid, propionic acid, and butanoic acid; and aromatic carboxylic acids such as benzoic acid. Among the examples of carboxylic acids listed above, acetic acid and propionic acid are preferable, and acetic acid is especially preferable.

A mole ratio of the carboxylic acid to the benzyl group of the benzyl compound is not particularly limited, provided that it is greater than the stoichiometric ratio, but is preferably from 1:1 to 20:1. If the foregoing mole ratio is less than 1:1, the quantity of carboxylic acid is insufficient, and it may be impossible to produce the benzyl ester efficiently. On the other hand, using carboxylic acid in a mole ratio exceeding 20:1 cannot be expected to obtain better yield, etc. than with a mole ratio in the foregoing range. Further, the large quantity of carboxylic acid used in this case leads to increase in the size of the reaction device and a recovery device for recovering the excess carboxylic acid, and may increase the production cost including recovery cost.

Benzyl ester is obtained by an oxidation reaction between the benzyl compound and the carboxylic acid in the presence of the foregoing catalyst. This oxidation reaction is carried out in a liquid or gaseous phase in the presence of oxygen gas (molecular oxygen). In other words, in the present invention, the oxidation reaction may be carried out in a liquid or gaseous phase, but it is preferable to carry it out in a liquid phase. The oxygen gas may be diluted with an inert gas such as nitrogen, helium, or argon gas. Further, air may be used as an oxygen-containing gas. The method of supplying the oxygen gas to the reaction system is not particularly limited.

The form of the reaction is not particularly limited, and may be continuous, batch, or semi-batch. When the reaction is, for example, a batch-type reaction, the catalyst and the starting materials may be placed in the reaction device all at once, and when the reaction is continuous, the catalyst may be placed in the reaction device in advance, or supplied continuously thereto along with the starting materials. Accordingly, the catalyst may be used in fixed bed, fluidized bed, or suspension bed reactions.

The quantity of catalyst with respect to the benzyl compound is not particularly limited, and may be set in accordance with the types and combination of the benzyl compound and the carboxylic acid, the composition of the catalyst, reaction conditions, etc.

Reaction conditions such as temperature, pressure, duration, etc. are not particularly limited, and may be set in accordance with the types and combination of the benzyl compound and the carboxylic acid, but a reaction temperature from 80° C. to 200° C. is suitable. If the reaction temperature is less than 80° C., the reaction rate is too slow, and it may not be possible to produce the benzyl ester efficiently. If the reaction temperature exceeds 200° C., on the other hand, side reactions such as combustion are likely to occur, and it may not be possible to produce the benzyl ester efficiently. Such a high reaction temperature also leads to corrosion of the reaction device by the carboxylic acid.

The reaction pressure may be reduced pressure, atmospheric pressure, or increased pressure, but when oxygen gas (undiluted oxygen gas) is used in the oxidation reaction, a pressure from atmospheric pressure to 50 kg/cm$^2$ (gauge pressure) is suitable, and when air is used in the oxidation reaction, a pressure from atmospheric pressure to 100 kg/cm$^2$ (gauge pressure) is suitable. A reaction pressure exceeding 100 kg/cm$^2$ is not industrially practical, from the point of view of equipment, etc.

In the oxidation reaction, when the benzyl compound and/or the carboxylic acid is liquid under the foregoing reaction conditions, use of a solvent is not particularly necessary, but when, for example, the reactants cannot be uniformly mixed, or when the reaction is violent, the reactants can be diluted using a solvent which is inert to the reaction.

Benzyl esters obtained by means of the production method according to the present invention, such as p-methylbenzyl acetate and p-xylylene diacetate, are compounds suitable for use as starting materials for synthetic resins such as polyester resin, as chemical substances such as aromatics and solvents, and as starting materials for producing such chemical substances. Incidentally, the method of separating and purifying the benzyl ester is not particularly limited.

Further, p-xylylene glycol, for example, which can be obtained by hydrolysis of p-xylylene diacetate, is a compound suitable for use as a starting material for synthetic fibers, synthetic resins, plasticizers, etc., or as a starting material for forming a compound material with polyurethane, carbon fibers, etc., and is particularly useful as a starting material for heat-resistant polymers. Incidentally, the method of hydrolysis of the benzyl ester is not particularly limited.

As discussed above, the oxidation catalyst according to the present invention has higher catalytic activity than conventional catalysts, and is suitable for use in an industrial production method. Consequently, an oxidation catalyst can be provided which is suitable for use in producing a benzyl ester such as p-methylbenzyl acetate or p-xylylene diacetate by reacting a benzyl compound such as p-xylene with a carboxylic acid such as acetic acid.

Further, with the preparation method according to the present invention, it is possible to prepare an oxidation catalyst having higher catalytic activity than conventional catalysts. Consequently, an oxidation catalyst can be prepared which is suitable for use in producing a benzyl ester by reacting a benzyl compound with a carboxylic acid.

Further, with the method of producing benzyl ester according to the present invention, it is possible to industrially produce benzyl ester efficiently and at low cost. For example, a benzyl ester such as p-methylbenzyl acetate or p-xylylene diacetate can be industrially produced, efficiently and at low cost, from p-xylene as the benzyl compound.

The following will explain the present invention in further detail by means of Examples and Comparative Examples, but the present invention is not intended to be limited to the following Examples. The term "turnover factor" (TOF) used in the following Examples is a measure of activity of the catalyst, and is defined as follows:

$$TOF = \frac{\text{(moles of monoester produced)} + 2\text{(moles of diester produced)}}{\text{(moles of palladium in catalyst)} \times \text{(reaction time (hours))}}$$

EXAMPLE 1

After immersing 60g of silica (product Silica Q-10, available from Fuji Silicia Chemical Co.) in 700 ml of a methyl alcohol solution containing 1.97 g of titanium (II) oxyacetylacetonate, the methyl alcohol was distilled out using an evaporator. The solid obtained thereby was dried at 120° C. for 12 hours, and then calcined at 600° C. for 3 hours, yielding, as the support, titania on silica. The quantity of titania in the support was 1% by weight with respect to the total weight.

Next, as the gold compound, 0.21 g of tetrachloroauric (III) acid tetrahydrate was dissolved in 200ml of water, and the resulting aqueous solution was heated to 60° C., and pH thereof was adjusted to 8.5 using an aqueous solution of sodium hydroxide. Then, as the surfactant, 0.28 g of sodium laurate was added to and dissolved in the foregoing aqueous solution. This yielded an aqueous solution of tetrachloroauric (III) acid. At 60° C., 5 g of the titania on silica was added to the foregoing aqueous solution, and then, by stirring for 30 minutes at the same temperature, the titania on silica was suspended and gold precipitate was affixed on the surface thereof.

Then the suspension was filtered, and the solid, i.e., the gold precipitate body, was washed in water and then dried at 120° C. for 8 hours. Next, the gold precipitate body was calcined at 400° C. for 3 hours, yielding, as the ultrafine gold particle body, gold on titania-silica. X-ray fluorescent analysis of the aqueous solution before and after preparation of the gold on titania-silica showed that the quantity of gold carried by the gold on titania-silica was 0.7% by weight with respect to the total weight.

Then, oxidation of a benzyl compound was performed using a catalyst including the gold on titania-silica. Specifically, 2.0 g of the gold on titania-silica (containing 0.0711 millimoles of gold), 0.0084 g of palladium acetate (available from Wako Junyaku Industries Co.) as the palladium compound (containing 0.0374 millimoles of palladium), 0.02 g of bismuth acetate oxide (available from Wako Junyaku Industries Co.) as a bismuth compound (third compound) (containing 0.0704 millimoles of bismuth), and 0.2 g of potassium acetate (available from Wako Junyaku Industries Co.) as an alkaline metal compound (third compound) (containing 2.0377 millimoles of potassium), were placed in a 100ml rotating autoclave. In other words, the catalyst according to the present invention was prepared by mixing the foregoing compounds, etc. in the autoclave.

Next, 5.0 g of p-xylene as the benzyl compound and 24.0 g of acetic acid as the carboxylic acid were added to the foregoing autoclave, which was then sealed. Then an oxidation reaction was performed by filling the autoclave with oxygen gas, pressurizing the interior thereof at 10 kg/cm$^2$ (gauge pressure), and then heating to 140° C. and stirring at 700 rpm for 2.5 hours. Incidentally, since oxygen gas was consumed during the reaction, pressure inside the autoclave gradually decreased, but no additional oxygen gas was supplied.

After cooling the autoclave, the contents were removed from the autoclave and the reaction mixture remaining after removal of the catalyst was analyzed by gas chromatography. The results showed that the reaction liquid contained, as benzyl esters, 2.37 g of p-methylbenzyl acetate and 1.62 g of p-xylylene diacetate. Accordingly, yield of p-methylbenzyl acetate was 30.6% by mole, and that of p-xylylene diacetate was 15.5% by mole. Further, the foregoing results showed that the turnover factor per unit of palladium in the catalyst per unit time was 320. The composition of the catalyst and the results obtained are shown in Tables 1 and 3 below.

EXAMPLE 2

After dissolving 0.104 g tetrachloroauric (III) acid tetrahydrate in 200 ml of water, an aqueous solution of tetrachloroauric (III) acid was prepared by the same method as in Example 1 above. Then, using as the support 5 g of titania (available from Norton Co.) instead of titania on silica, the method of Example 1 above was used to obtain gold on titania as the ultrafine gold particle body. X-ray fluorescent analysis of the aqueous solution before and after preparation of the gold on titania showed that the quantity of gold carried by the gold on titania was 0.9% by weight with respect to the total weight.

Then an oxidation reaction was performed under the same reaction conditions as in Example 1 above, except for using 2.0 g of the gold on titania, and changing the quantity of palladium acetate to 0.0042 g. The composition of the reaction liquid was then analyzed. The results showed that the reaction liquid contained 1.97 g of p-methylbenzyl acetate and 1.19 g of p-xylylene diacetate. Accordingly, yield of p-methylbenzyl acetate was 25.5% by mole, and that of p-xylylene diacetate was 11.4% by mole. Further, the turnover factor was 488. The composition of the catalyst and the results obtained are shown in Tables 1 and 3 below.

EXAMPLE 3

After dissolving 0.104 g tetrachloroauric (III) acid tetrahydrate in 200 ml of water, an aqueous solution of tetrachloroauric (III) acid was prepared by the same method as in Example 1 above. Then, using as the support 5 g of titanosilicate (TS-1) instead of titania on silica, the method of Example 1 above was used to obtain gold on titanosilicate as the ultrafine gold particle body. X-ray fluorescent analysis of the aqueous solution before and after preparation of the gold on titanosilicate showed that the quantity of gold carried by the gold on titanosilicate was 0.6% by weight with respect to the total weight.

Then an oxidation reaction was performed under the same reaction conditions as in Example 1 above, except for using 2.0 g of the gold on titanosilicate, and changing the quantity of palladium acetate to 0.0042 g. The composition of the reaction liquid was then analyzed. The results showed that the reaction liquid contained 1.15 g of p-methylbenzyl acetate and 0.64 g of p-xylylene diacetate. Accordingly, yield of p-methylbenzyl acetate was 14.9% by mole, and that of p-xylylene diacetate was 6.1% by mole. Further, the turnover factor was 273. The composition of the catalyst and the results obtained are shown in Tables 1 and 3 below.

EXAMPLE 4

First, 0.11 g of tetrachloroauric (III) acid tetrahydrate was dissolved in 200 ml of water, and the resulting aqueous solution was heated to 60° C., and pH thereof was adjusted to 8.5 using an aqueous solution of sodium hydroxide. Then 0.013 g of tetraammine palladium dichloride as the palladium compound and 0.14 g of sodium laurate were added to and dissolved in the foregoing aqueous solution. This yielded an aqueous solution of tetrachloroauric (III) acid. At 60° C., 5 g of the titania on silica used in Example 1 was added to the foregoing aqueous solution, and then, by stirring for 1 hour at the same temperature, the titania on silica was suspended, and palladium precipitate and gold precipitate were affixed on the surface thereof.

Then the suspension was filtered, and the resulting filtrate, i.e., a palladium/gold precipitate body, was washed in water and then dried at 120° C. for 8 hours. Next, the palladium/gold precipitate body was calcined at 400° C. for 3 hours, yielding, as the ultrafine gold particle body, palladium-gold on titania-silica. X-ray fluorescent analysis of the aqueous solution before and after preparation of the palladium-gold on titania-silica showed that the palladium-gold on titania-silica carried 0.1° C. by weight of palladium and 0.35% by weight of gold, with respect to the total weight.

Then, 4.0 g of the palladium-gold on titania-silica (containing 0.0376 millimoles of palladium and 0.0711 millimoles of gold), 0.02 g of bismuth acetate oxide (available from Wako Junyaku Industries Co.), and 0.2 g of potassium acetate (available from Wako Junyaku Industries Co.), were placed in a 100 ml rotating autoclave. In other words, the catalyst according to the present invention was prepared by mixing the foregoing compounds, etc. in the autoclave.

Then an oxidation reaction was performed under the same reaction conditions as in Example 1 above, and the composition of the reaction liquid was analyzed. The results showed that the reaction liquid contained 1.92 g of p-methylbenzyl acetate and 1.21 g of p-xylylene diacetate. Accordingly, yield of p-methylbenzyl acetate was 24.8% by mole, and that of p-xylylene diacetate was 11.5% by mole. Further, the turnover factor was 245. The composition of the catalyst and the results obtained are shown in Tables 1 and 3 below.

EXAMPLE 5

An oxidation reaction was performed under the same reaction conditions as in Example 1 above, except for using 0.023 g of molybdenic acid (containing 0.0704 millimoles of molybdenum) as a molybdenum compound (third compound) instead of the bismuth acetate oxide. The composition of the reaction liquid was then analyzed. The results showed that the reaction liquid contained 0.15 g of p-methylbenzyl acetate and 0.10 g of p-xylylene diacetate. Accordingly, yield of p-methylbenzyl acetate was 1.9% by mole, and that of p-xylylene diacetate was 1.0% by mole. Further, the turnover factor was 20. The composition of the catalyst and the results obtained are shown in Tables 1 and 3 below.

EXAMPLE 6

An oxidation reaction was performed under the same reaction conditions as in Example 1 above, except for using 0.022 g of iron nitrate (containing 0.0704 millimoles of iron) as an iron compound (third compound) instead of the bismuth acetate oxide. The composition of the reaction liquid was then analyzed. The results showed that the reaction liquid contained 0.22 g of p-methylbenzyl acetate and 0.16 g of p-xylylene diacetate. Accordingly, yield of p-methylbenzyl acetate was 2.8% by mole, and that of p-xylylene diacetate was 1.5% by mole. Further, the foregoing results showed that the turnover factor was 29. The composition of the catalyst and the results obtained are shown in Tables 1 and 3 below.

EXAMPLE 7

An oxidation reaction was performed under the same reaction conditions as in Example 1 above, except for using 4.3 g of toluene, instead of p-xylene, as the benzyl compound. The composition of the reaction liquid was then analyzed. The results showed that the reaction liquid contained 4.9 g of benzyl acetate as the benzyl ester. Accordingly, yield of benzyl acetate was 69.3% by mole. Further, the foregoing results showed that the turnover factor was 345. The composition of the catalyst and the results obtained are shown in Tables 1 and 3 below.

EXAMPLE 8

An oxidation reaction was performed under the same reaction conditions as in Example 1 above, except for using 5.0 g of p-methylbenzyl acetate, instead of p-xylene, as the benzyl compound, and changing the reaction time to 3.0 hours. The composition of the reaction liquid was then analyzed. The results showed that the reaction liquid contained 0.50 g of p-xylylene diacetate as the benzyl ester. Accordingly, yield of p-xylylene diacetate was 7.3% by mole. Further, the turnover factor was 24. The composition of the catalyst and the results obtained are shown in Tables 1 and 3 below.

EXAMPLE 9

An oxidation reaction was performed under the same reaction conditions as in Example 1 above, except for using 29.6 g of propionic acid, instead of acetic acid, as the carboxylic acid, and changing the reaction time to 7.0 hours. The composition of the reaction liquid was then analyzed. The results showed that the reaction liquid contained, as benzyl esters, 1.92 g of p-methylbenzyl propionate and 1.32 g of p-xylylene dipropionate. Accordingly, yield of p-methylbenzyl propionate was 22.9% by mole, and that of p-xylylene dipropionate was 11.2% by mole. Further, the turnover factor was 81. The composition of the catalyst and the results obtained are shown in Tables 2 and 3 below.

EXAMPLE 10

An oxidation reaction was performed under the same reaction conditions as in Example 1 above, except for changing the quantity of palladium acetate to 0.0005 g (containing 0.0023 millimoles of palladium), and changing the reaction time to 5.0 hours. The composition of the reaction liquid was then analyzed. The results showed that yield of p-methylbenzyl acetate was 8.0% by mole, and that of p-xylylene diacetate was 5.0% by mole. Further, the turnover factor was 753. The composition of the catalyst and the results obtained are shown in Tables 2 and 3 below.

EXAMPLE 11

First, as the ultrafine gold particle body, palladium-gold on titania was obtained by the same method as in Example 4 above, except for changing the quantity of tetraammine palladium dichloride to 0.062 g, and using 5 g of titania, instead of titania on silica, as the support. X-ray fluorescent analysis of the aqueous solution before and after preparation of the palladium-gold on titania showed that the palladium-gold on titania carried 0.5% by weight of palladium and 1.0% by weight of gold, with respect to the total weight.

Then, 1.0 g of the palladium-gold on titania (containing 0.047 millimoles of palladium and 0.051 millimoles of gold), and 0.02 g of lanthanum (III) acetate sesquihydrate (containing 0.0583 millimoles of lanthanum) as a lanthanum compound (third compound) were placed in a 100 ml rotating autoclave. In other words, the catalyst according to the present invention was prepared by mixing the foregoing compounds, etc. in the autoclave.

Then an oxidation reaction was performed under the same reaction conditions as in Example 1 above, except for changing the quantities of p-xylene and acetic acid to 10.0 g and 12.0 g, respectively, and changing the reaction time to 1.0 hour. The composition of the reaction liquid was then analyzed. The results showed that the reaction liquid contained 0.47 g of p-methylbenzyl acetate and 0.35 g of p-xylylene diacetate. Accordingly, yield of p-methylbenzyl acetate was 3.05% by mole, and that of p-xylylene diacetate was 1.66% by mole. Further, the turnover factor was 128. The composition of the catalyst and the results obtained are shown in Tables 2 and 3 below.

EXAMPLE 12

An oxidation reaction was performed under the same reaction conditions as in Example 11 above, except for using 0.02 g of zinc (II) acetate dihydrate (containing 0.0993 millimoles of zinc) as a zinc compound (third compound) instead of the lanthanum (III) acetate sesquihydrate. The composition of the reaction liquid was then analyzed. The results showed that the reaction liquid contained 0.53 g of p-methylbenzyl acetate and 0.36 g of p-xylylene diacetate. Accordingly, yield of p-methylbenzyl acetate was 3.44% by mole, and that of p-xylylene diacetate was 1.74% by mole. Further, the turnover factor was 139. The composition of the catalyst and the results obtained are shown in Tables 2 and 3 below.

EXAMPLE 13

An oxidation reaction was performed under the same reaction conditions as in Example 11 above, except for using 0.02 g of nickel (II) acetate tetrahydrate (containing 0.0804 millimoles of nickel) as a nickel compound (third compound) instead of the lanthanum (III) acetate sesquihydrate. The composition of the reaction liquid was then analyzed. The results showed that the reaction liquid contained 0.50 g of p-methylbenzyl acetate and 0.34 g of p-xylylene diacetate. Accordingly, yield of p-methylbenzyl acetate was 3.22% by mole, and that of p-xylylene diacetate was 1.63% by mole. Further, the turnover factor was 130. The composition of the catalyst and the results obtained are shown in Tables 2 and 3 below.

EXAMPLE 14

An oxidation reaction was performed under the same reaction conditions as in Example 11 above, except for using 0.02 g of barium (II) acetate monohydrate (containing 0.0731 millimoles of barium) as an alkaline earth metal compound (third compound) instead of the lanthanum (III) acetate sesquihydrate. The composition of the reaction liquid was then analyzed. The results showed that the reaction liquid contained 0.60 g of p-methylbenzyl acetate and 0.43 g of p-xylylene diacetate. Accordingly, yield of p-methylbenzyl acetate was 3.89% by mole, and that of p-xylylene diacetate was 2.04% by mole. Further, the turnover factor was 160. The composition of the catalyst and the results obtained are shown in Tables 2 and 3 below.

EXAMPLE 15

An oxidation reaction was performed under the same reaction conditions as in Example 11 above, except for using 0.20 g of potassium acetate (containing 2.0377 millimoles of potassium) as an alkaline metal compound (third compound) instead of the lanthanum (III) acetate sesquihydrate. The composition of the reaction liquid was then analyzed. The results showed that the reaction liquid contained 0.44 g of p-methylbenzyl acetate and 0.39 g of p-xylylene diacetate. Accordingly, yield of p-methylbenzyl acetate was 2.85% by mole, and that of p-xylylene diacetate was 1.86% by mole. Further, the turnover factor was 132. The composition of the catalyst and the results obtained are shown in Tables 2 and 3 below.

Comparative Example 1

After dissolving 0.11 g tetrachloroauric (III) acid tetrahydrate in 200 ml of water, 5 g of the titania on silica used in Example 1 above was added to the foregoing aqueous solution. Next, this mixture was heated to evaporate the water and solidify the mixture, yielding titania-silica with gold precipitate fixed on the surface thereof by impregnation. However, the gold precipitate was not in the form of ultrafine particles. The quantity of gold carried by the comparative gold on titania-silica obtained as above was 1.0% by weight with respect to the total weight.

Next, 2.0 g of the comparative gold on titania-silica obtained above (containing 0.1015 millimoles of gold), 0.0084 g of palladium acetate, 0.02 g of bismuth acetate oxide, and 0.2 g of potassium acetate were placed in a 100 ml rotating autoclave. In other words, a comparative catalyst was prepared by mixing the foregoing compounds, etc. in the autoclave.

Then an oxidation reaction was performed under the same reaction conditions as in Example 1 above, and the composition of the resulting reaction liquid was analyzed. The results showed that the reaction liquid contained almost no p-methylbenzyl acetate and p-xylylene diacetate. In other words, it was found that the comparative catalyst had almost no catalytic activity. The composition of the catalyst and the results obtained are shown in Tables 2 and 3 below.

Comparative Example 2

An oxidation reaction was performed under the same reaction conditions as in Example 1 above, except that bismuth acetate oxide and potassium acetate were not used, and the composition of the reaction liquid was then analyzed. In other words, an oxidation reaction was performed using a comparative catalyst not containing the third compound. The results showed that the reaction liquid contained almost no p-methylbenzyl acetate or p-xylylene diacetate. In other words, it was found that the comparative catalyst had almost no catalytic activity. The composition of the catalyst and the results obtained are shown in Tables 2 and 3 below.

TABLE 1

| | COMPOSITION OF CATALYST | | | | | | |
|---|---|---|---|---|---|---|---|
| | PALLADIUM (MILLIMOLES) | GOLD (MILLIMOLES) | Au/Pd | THIRD COMPOUND | MILLIMOLES OF THIRD COMPOUND | THIRD COMPOUND/Pd | SUPPORT |
| EXAMPLES | | | | | | | |
| 1 | 0.0374 | 0.0711 | 1.8998 | BISMUTH POTASSIUM | 0.0704 2.0377 | 1.8821 54.48 | TiO$_2$—SiO$_2$ |
| 2 | 0.0187 | 0.0914 | 4.8871 | BISMUTH POTASSIUM | 0.0704 2.0377 | 3.7642 108.97 | TiO$_2$ |
| 3 | 0.0187 | 0.0609 | 3.2581 | BISMUTH POTASSIUM | 0.0704 2.0377 | 3.7642 108.97 | TITANO-SILICATE |
| 4 | 0.0376 | 0.0711 | 1.8907 | BISMUTH POTASSIUM | 0.0704 2.0377 | 1.8731 54.19 | TiO$_2$—SiO$_2$ |
| 5 | 0.0374 | 0.0711 | 1.8998 | MOLYBDENUM POTASSIUM | 0.0704 2.0377 | 1.8821 54.48 | TiO$_2$—SiO$_2$ |
| 6 | 0.0374 | 0.0711 | 1.8998 | IRON POTASSIUM | 0.0704 2.0377 | 1.8821 54.48 | TiO$_2$—SiO$_2$ |
| 7 | 0.0374 | 0.0711 | 1.8998 | BISMUTH POTASSIUM | 0.0704 2.0377 | 1.8821 54.48 | TiO$_2$—SiO$_2$ |
| 8 | 0.0374 | 0.0711 | 1.8998 | BISMUTH POTASSIUM | 0.0704 2.0377 | 1.8821 54.48 | TiO$_2$—SiO$_2$ |

TABLE 2

| | COMPOSITION OF CATALYST | | | | | | |
|---|---|---|---|---|---|---|---|
| | PALLADIUM (MILLIMOLES) | GOLD (MILLIMOLES) | Au/Pd | THIRD COMPOUND | MILLIMOLES OF THIRD COMPOUND | THIRD COMPOUND/Pd | SUPPORT |
| EXAMPLES | | | | | | | |
| 9 | 0.0374 | 0.0711 | 1.8998 | BISMUTH POTASSIUM | 0.0704 2.0377 | 1.8821 54.48 | TiO$_2$—SiO$_2$ |
| 10 | 0.0023 | 0.0711 | 30.91 | BISMUTH POTASSIUM | 0.0704 2.0377 | 30.61 885.96 | TiO$_2$—SiO$_2$ |
| 11 | 0.047 | 0.051 | 1.085 | LANTHANUM | 0.0583 | 1.2405 | TiO$_2$ |
| 12 | 0.047 | 0.051 | 1.085 | ZINC | 0.0993 | 2.1121 | TiO$_2$ |
| 13 | 0.047 | 0.051 | 1.085 | NICKEL | 0.0804 | 1.7105 | TiO$_2$ |
| 14 | 0.047 | 0.051 | 1.085 | BARIUM | 0.0731 | 1.5563 | TiO$_2$ |
| 15 | 0.047 | 0.051 | 1.085 | POTASSIUM | 2.0377 | 43.36 | TiO$_2$ |
| COMPARATIVE EXAMPLES | | | | | | | |
| 1 | 0.0374 | 0.1015[a] | 2.7140 | BISMUTH POTASSIUM | 0.0704 2.0377 | 1.8821 54.48 | TiO$_2$—SiO$_2$ |
| 2 | 0.0374 | 0.0711 | 1.8998 | — | — | — | TiO$_2$—SiO$_2$ |

[a] NOT ULTRAFINE PARTICLES

TABLE 3

| | REACTION | YIELD OF BENZYL ESTER | | | | TURNOVER |
|---|---|---|---|---|---|---|
| | TIME (hr) | MONOESTER | (MOL %) | DIESTER | (MOL %) | FACTOR |
| EXAMPLES | | | | | | |
| 1 | 2.5 | p-METHYLBENZYL ACETATE | 30.6 | p-XYLYLENE DIACETATE | 15.5 | 320 |
| 2 | 2.5 | p-METHYLBENZYL ACETATE | 25.5 | p-XYLYLENE DIACETATE | 11.4 | 488 |
| 3 | 2.5 | p-METHYLBENZYL ACETATE | 14.9 | p-XYLYLENE DIACETATE | 6.1 | 273 |
| 4 | 2.5 | p-METHYLBENZYL ACETATE | 24.8 | p-XYLYLENE DIACETATE | 11.5 | 245 |
| 5 | 2.5 | p-METHYLBENZYL ACETATE | 1.9 | p-XYLYLENE DIACETATE | 1.0 | 20 |
| 6 | 2.5 | p-METHYLBENZYL ACETATE | 2.8 | p-XYLYLENE DIACETATE | 1.5 | 29 |
| 7 | 2.5 | BENZYL ACETATE | 69.3 | — | — | 345 |
| 8 | 3.0 | — | — | p-XYLYLENE DIACETATE | 7.3 | 24 |
| 9 | 7.0 | p-METHYLBENZYL PROPIONATE | 22.9 | p-XYLYLENE DIPROPIONATE | 11.2 | 81 |
| 10 | 5.0 | p-METHYLBENZYL ACETATE | 8.0 | p-XYLYLENE DIACETATE | 5.0 | 753 |

TABLE 3-continued

| | REACTION TIME (hr) | YIELD OF BENZYL ESTER | | | | TURNOVER FACTOR |
|---|---|---|---|---|---|---|
| | | MONOESTER | (MOL %) | DIESTER | (MOL %) | |
| 11 | 1.0 | p-METHYLBENZYL ACETATE | 3.05 | p-XYLYLENE DIACETATE | 1.66 | 128 |
| 12 | 1.0 | p-METHYLBENZYL ACETATE | 3.44 | p-XYLYLENE DIACETATE | 1.74 | 139 |
| 13 | 1.0 | p-METHYLBENZYL ACETATE | 3.22 | p-XYLYLENE DIACETATE | 1.63 | 130 |
| 14 | 1.0 | p-METHYLBENZYL ACETATE | 3.89 | p-XYLYLENE DIACETATE | 2.04 | 160 |
| 15 | 1.0 | p-METHYLBENZYL ACETATE | 2.85 | p-XYLYLENE DIACETATE | 1.86 | 132 |
| COMPARATIVE EXAMPLES | | | | | | |
| 1 | 2.5 | | | TRACE | | — |
| 2 | 2.5 | | | TRACE | | — |

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations, provided such variations do not depart from the spirit of the present invention or exceed the scope of the patent claims set forth below.

What is claimed is:

1. An oxidation catalyst for oxidation, containing:
either one of (i) palladium and ultrafine gold particles and (ii) ultrafine palladium-gold particles, said ultrafine particles respectively having diameters of the nanometer (nm) order, and at least one element selected from the group consisting of alkali metals and the elements of Groups IIA, IIIA, VIA, IIB, VB, and VIII of the Periodic Table.

2. The oxidation catalyst set forth in claim 1, wherein:
said at least one element is at least one element selected from the group consisting of bismuth, molybdenum, iron, nickel, zinc, lanthanum, an alkaline earth metal, and alkali metal.

3. The oxidation catalyst set forth in claim 1, wherein:
a quantity of said at least one element with respect to total weight of said catalyst is from 0.0001 weight percent through 10 weight percent, inclusive.

4. The oxidation catalyst set forth in claim 1, wherein:
said ultrafine gold particles are supported on a support.

5. The oxidation catalyst set forth in claim 4, wherein:
said support is a porous inorganic substance.

6. The oxidation catalyst set forth in claim 4, wherein:
said support includes at least one inorganic substance selected from the group consisting of titanium oxide, zirconium oxide, and aluminum oxide.

7. A method for preparing an oxidation catalyst for oxidation, comprising the steps of:
(a) heat processing a gold compound at a temperature of 150° C. through 800° C., inclusive, to obtain ultrafine gold particles, said ultrafine particles respectively having diameters on the nanometer (nm) order; and
(b) mixing the ultrafine gold particles obtained in step (a) with a palladium compound and a compound containing at least one element selected from the group consisting of alkali metals and the elements of Groups IIA, IIIA, VIA, IIB, VB, and VIII of the Periodic Table.

8. A method for preparing an oxidation catalyst for oxidation, comprising the steps of:
(a) heat processing a gold compound and a palladium compound at a temperature of 150° C. through 800° C., inclusive, to obtain a mixture containing ultrafine palladium-gold particles, said ultrafine particles respectively having diameters on the nanometer (nm) order; and
(b) mixing the ultrafine palladium-gold particles obtained in step (a) with a compound containing at least one element selected from the group consisting of alkali metals and the elements of Groups IIA, IIIA, VIA, IIB, VB, and VIII of the Periodic Table.

9. A method for preparing an oxidation catalyst for oxidation, comprising the steps of:
(a) immersing a carrier in an aqueous solution having a pH of 6 to 10 in the presence of an interfacial active agent;
(b) separating a gold precipitate on the carrier;
(c) heat processing the carrier at a temperature of 150° C. through 800° C., inclusive, to obtain ultrafine gold particles, said ultrafine particles respectively having diameters on the nanometer (nm) order; and
(d) mixing the ultrafine gold particles obtained in step (c) with a palladium compound and a compound containing at least one element selected from the group consisting of alkali metals and the elements of Groups IIA, IIIA, VIA, IIB, VB and VIII of the Periodic Table.

10. A method for preparing an oxidation catalyst for oxidation, comprising the steps of:
(a) immersing a carrier in an aqueous solution having a pH of 6 to 10 in the presence of an interfacial agent;
(b) separating a gold precipitate and a palladium precipitate on the carrier;
(c) heat processing the carrier at a temperature of 150° C. through 800° C., inclusive, to obtain ultrafine palladium-gold particles, said ultrafine particles respectively having diameters on the nanometer (nm) order; and
(d) mixing the palladium-gold particles obtained in step (c) with a compound containing at least one element selected from the group consisting of alkali metals and the elements of Groups IIA, IIIA, VIA, IIB, VB and VIII of the Periodic Table.

* * * * *